US009743902B2

(12) United States Patent
Katsumata

(10) Patent No.: US 9,743,902 B2
(45) Date of Patent: Aug. 29, 2017

(54) IMAGE PROCESSING APPARATUS, IMAGE PROCESSING METHOD, RADIATION IMAGING SYSTEM, AND STORAGE MEDIUM

(71) Applicant: CANON KABUSHIKI KAISHA, Tokyo (JP)

(72) Inventor: Shinya Katsumata, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/064,536

(22) Filed: Oct. 28, 2013

(65) Prior Publication Data

US 2014/0133637 A1    May 15, 2014

(30) Foreign Application Priority Data

Nov. 9, 2012 (JP) ................................. 2012-247749

(51) Int. Cl.
*G06K 9/00* (2006.01)
*A61B 6/00* (2006.01)

(52) U.S. Cl.
CPC .................... *A61B 6/585* (2013.01)

(58) Field of Classification Search
CPC ........ H04N 1/6072; G06T 2207/10116; G06T 382/131; G06T 382/132
See application file for complete search history.

(56) References Cited

U.S. PATENT DOCUMENTS

| 4,746,571 A * | 5/1988 | Kelly ................ G01N 23/2252 250/310 |
| 4,810,881 A | 3/1989 | Berger et al. ............ 250/370.01 |
| 5,132,539 A | 7/1992 | Kwasnick et al. ........ 250/361 R |
| 5,369,679 A * | 11/1994 | Sliski ................... A61N 5/1001 378/205 |
| 5,381,014 A * | 1/1995 | Jeromin ............ H01L 27/14609 250/370.09 |
| 5,396,072 A | 3/1995 | Schiebel et al. ......... 250/370.09 |
| 5,418,377 A | 5/1995 | Tran et al. ................. 250/483.1 |
| 5,594,807 A * | 1/1997 | Liu ........................ G06T 5/008 382/128 |

(Continued)

FOREIGN PATENT DOCUMENTS

| JP | 2001-351091 | 12/2001 |
| JP | 2010-012105 | 1/2010 |

*Primary Examiner* — Iman K Kholdebarin
(74) *Attorney, Agent, or Firm* — Fitzpatrick, Cella, Harper & Scinto

(57) ABSTRACT

A radiation imaging system including an X-ray sensor with a plurality of sensor chips disposed next to each other and an image processing apparatus which performs abnormality determination concerning a white image obtained by irradiating the X-ray sensor with X-rays without any object disposed between the X-ray sensor and an X-ray generator, the system includes: an area acquisition unit configured to acquire information of partial areas of the white image which respectively correspond to the plurality of sensor chips; a distribution acquisition unit configured to acquire distribution information representing variation in pixel value for each of the acquired partial areas; and a determination unit configured to determine, based on the distribution information, whether abnormality is included in the white image.

27 Claims, 7 Drawing Sheets

(56) References Cited

U.S. PATENT DOCUMENTS

| | | | | |
|---|---|---|---|---|
| 5,640,469 A * | 6/1997 | Lewins | G06T 5/009 | 348/672 |
| 5,751,844 A * | 5/1998 | Bolin | G06T 5/40 | 348/221.1 |
| 5,873,824 A * | 2/1999 | Doi | G06K 9/00 | 128/925 |
| 5,875,258 A * | 2/1999 | Ortyn | G01N 35/00594 | 128/922 |
| 6,018,565 A * | 1/2000 | Ergun | A61B 6/4405 | 348/E5.081 |
| 6,192,163 B1 * | 2/2001 | Murayama | G06T 5/20 | 382/199 |
| 6,468,218 B1 * | 10/2002 | Chen | A61B 6/469 | 128/916 |
| 6,658,080 B1 * | 12/2003 | Poole | A61B 5/7445 | 378/4 |
| 6,718,056 B1 * | 4/2004 | Bothorel | G06T 5/009 | 382/128 |
| 6,757,442 B1 * | 6/2004 | Avinash | G06T 5/004 | 382/168 |
| 6,813,040 B1 * | 11/2004 | Uchino | H04N 1/2158 | 358/1.9 |
| 6,819,786 B2 * | 11/2004 | Hirai | G06T 7/0002 | 382/132 |
| 6,993,167 B1 * | 1/2006 | Skladnev | A61B 5/444 | 382/128 |
| 6,993,183 B2 * | 1/2006 | Inoue | G06T 7/0081 | 345/596 |
| 7,310,444 B2 * | 12/2007 | Inoue | G06T 7/0081 | 358/3.23 |
| 7,394,925 B2 * | 7/2008 | Hayashida | A61B 6/583 | 378/62 |
| 7,599,541 B2 * | 10/2009 | Hayashida | H04N 5/3597 | 378/91 |
| 7,817,196 B1 * | 10/2010 | Pinto | H04N 5/217 | 348/241 |
| 7,835,588 B2 * | 11/2010 | Parkkinen | G06T 5/009 | 382/168 |
| 8,090,165 B2 * | 1/2012 | Jiang | G06T 5/009 | 382/128 |
| 8,098,932 B2 * | 1/2012 | Wu | G09G 5/02 | 382/167 |
| 8,131,108 B2 * | 3/2012 | Neuman | G06T 5/009 | 382/167 |
| 8,136,721 B2 * | 3/2012 | Prakash | G06K 9/03 | 235/379 |
| 8,184,177 B2 * | 5/2012 | Kakuta | H04N 1/608 | 348/223.1 |
| 8,517,608 B1 * | 8/2013 | Arnold | A61B 6/032 | 378/207 |
| 8,606,052 B2 * | 12/2013 | Mercur'ev | H04N 5/3653 | 382/128 |
| 8,781,175 B2 * | 7/2014 | Wang | G06K 9/00624 | 382/112 |
| 8,797,347 B2 * | 8/2014 | Miyachi | H04N 5/147 | 345/590 |
| 8,923,571 B2 * | 12/2014 | Dixon | H04N 1/00015 | 358/1.9 |
| 8,965,120 B2 * | 2/2015 | Yamanaka | G06T 5/003 | 382/167 |
| 8,995,725 B2 * | 3/2015 | Li | G06K 9/00624 | 382/112 |
| 9,384,519 B1 * | 7/2016 | Tripp | G06F 17/30271 | |
| 2001/0015407 A1 * | 8/2001 | Tsujii | G06T 5/008 | 250/252.1 |
| 2001/0033678 A1 * | 10/2001 | Hirai | G06T 7/0002 | 382/128 |
| 2002/0159633 A1 * | 10/2002 | Inoue | G06T 7/136 | 382/170 |
| 2003/0095698 A1 * | 5/2003 | Kawano | G06T 7/12 | 382/132 |
| 2003/0205676 A1 * | 11/2003 | Nelson | A61B 6/4233 | 250/370.09 |
| 2004/0012700 A1 * | 1/2004 | Okisu | H04N 1/4072 | 348/333.01 |
| 2004/0101091 A1 * | 5/2004 | Rosner | G01N 23/04 | 378/19 |
| 2004/0170308 A1 * | 9/2004 | Belykh | G06T 5/007 | 382/128 |
| 2004/0217294 A1 * | 11/2004 | Zur | G01T 1/2018 | 250/370.09 |
| 2004/0233317 A1 * | 11/2004 | Matsushita | G02B 21/365 | 348/333.02 |
| 2004/0234113 A1 * | 11/2004 | Miga | G06T 7/0012 | 382/128 |
| 2005/0025357 A1 * | 2/2005 | Landwehr | A01M 1/026 | 382/170 |
| 2005/0036703 A1 * | 2/2005 | Hannequin | G06K 9/40 | 382/260 |
| 2005/0047552 A1 * | 3/2005 | Arai | A61B 6/032 | 378/207 |
| 2005/0047639 A1 * | 3/2005 | Hayashida | H04N 5/3597 | 382/132 |
| 2005/0109927 A1 * | 5/2005 | Takenaka | G01T 1/2928 | 250/252.1 |
| 2005/0285955 A1 * | 12/2005 | Utz | H04N 9/045 | 348/265 |
| 2006/0025670 A1 * | 2/2006 | Kim | A61B 3/00 | 600/407 |
| 2006/0029274 A1 * | 2/2006 | Inoue | G06T 7/0081 | 382/170 |
| 2006/0233455 A1 * | 10/2006 | Cheng | G01R 33/56563 | 382/274 |
| 2006/0239581 A1 * | 10/2006 | Neuman | G06T 5/009 | 382/274 |
| 2007/0076937 A1 * | 4/2007 | Spahn | A61B 6/542 | 382/132 |
| 2007/0081707 A1 * | 4/2007 | Sirohey | G06F 19/3431 | 382/128 |
| 2007/0250274 A1 * | 10/2007 | Volkov | C12Q 1/6813 | 702/22 |
| 2007/0274457 A1 * | 11/2007 | Dunham | A61B 6/032 | 378/207 |
| 2008/0018643 A1 * | 1/2008 | Feilkas | G06T 7/50 | 345/420 |
| 2008/0123952 A1 * | 5/2008 | Parkkinen | G06T 5/009 | 382/168 |
| 2008/0123986 A1 * | 5/2008 | Jiang | G06T 5/009 | 382/255 |
| 2008/0166035 A1 * | 7/2008 | Qian | G06T 7/0012 | 382/133 |
| 2008/0240558 A1 * | 10/2008 | Li | H04N 1/00045 | 382/167 |
| 2008/0279472 A1 * | 11/2008 | Hannequin | G06T 5/10 | 382/260 |
| 2008/0285851 A1 * | 11/2008 | Wu | G09G 5/02 | 382/167 |
| 2009/0087045 A1 * | 4/2009 | Partain | G06T 7/0012 | 382/128 |
| 2009/0268053 A1 * | 10/2009 | Wang | H01L 27/14625 | 348/229.1 |
| 2011/0063469 A1 * | 3/2011 | Omi | H04N 5/23293 | 348/222.1 |
| 2012/0070047 A1 * | 3/2012 | Johnson | G06T 11/001 | 382/128 |
| 2012/0106808 A1 * | 5/2012 | Morioka | G06K 9/0008 | 382/125 |
| 2012/0209526 A1 * | 8/2012 | Imhof | G01V 1/306 | 702/5 |
| 2012/0328189 A1 * | 12/2012 | Usher | G06F 17/30256 | 382/165 |
| 2013/0179389 A1 * | 7/2013 | Malle | G06F 17/30592 | 706/47 |
| 2013/0202204 A1 * | 8/2013 | Yamanaka | G06T 5/003 | 382/167 |
| 2013/0265461 A1 * | 10/2013 | Kano | G06T 3/4015 | 348/222.1 |

(56) References Cited

U.S. PATENT DOCUMENTS

| | | | | |
|---|---|---|---|---|
| 2014/0105480 A1* | 4/2014 | Motomura | ............ | G06T 7/0012 |
| | | | | 382/133 |
| 2014/0119500 A1* | 5/2014 | Akahori | ................. | A61B 6/025 |
| | | | | 378/17 |
| 2014/0133637 A1* | 5/2014 | Katsumata | ............. | A61B 6/585 |
| | | | | 378/207 |
| 2014/0140604 A1* | 5/2014 | Carton | ................... | A61B 6/481 |
| | | | | 382/132 |
| 2014/0294274 A1* | 10/2014 | Wang | ........................ | G06T 7/35 |
| | | | | 382/131 |
| 2014/0294277 A1* | 10/2014 | Katsumata | ............. | G06T 5/007 |
| | | | | 382/132 |
| 2014/0363085 A1* | 12/2014 | Li | ...................... | G06K 9/00624 |
| | | | | 382/190 |
| 2015/0085979 A1* | 3/2015 | Zheng | ................... | A61B 6/584 |
| | | | | 378/62 |
| 2015/0092035 A1* | 4/2015 | Yamamoto | ............. | G02B 21/06 |
| | | | | 348/68 |
| 2015/0146925 A1* | 5/2015 | Son | ................... | G06K 9/00624 |
| | | | | 382/103 |
| 2015/0310597 A1* | 10/2015 | Ohguri | ................. | H04N 5/2254 |
| | | | | 382/275 |
| 2017/0000443 A1* | 1/2017 | Katsumata | ........... | A61B 6/5282 |

* cited by examiner

IMAGE PROCESSING APPARATUS, IMAGE PROCESSING METHOD, RADIATION IMAGING SYSTEM, AND STORAGE MEDIUM

BACKGROUND OF THE INVENTION

Field of the Invention

The present invention relates to an image processing apparatus, an image processing method, a radiation imaging system, and a storage medium.

Description of the Related Art

It is possible to acquire a radiation image of an object by irradiating the object with radiation and detecting the intensity distribution of the radiation transmitted through the object. The most common method as a method of acquiring a radiation image is to combine a so-called "fluorescent screen" (or "intensifying screen"), which emits fluorescence upon irradiation with radiation, with a silver halide film first and then irradiate them with radiation through an object. With this operation, the fluorescent screen converts the radiation into visible light to form a latent image of the object on the silver halide film. Thereafter, chemically treating the silver halide film on which the latent image of the object is formed can obtain a visible image of the object (a radiation image of the object) on the silver halide film. The radiation image obtained by such a radiation image acquisition method is an analog photograph, which is used for image diagnosis, examination, and the like.

On the other hand, it has begun to use a computed radiography apparatus (to be referred as a "CR apparatus" hereafter) using an imaging plate (to be referred to as an "IP" hereinafter) coated with a photostimulable phosphor as a phosphor. In this CR apparatus, secondarily exciting the IP primarily excited by irradiation with radiation by using visible light such as red laser light will generate light called photostimulable fluorescence. Detecting this fluorescence by a photosensor such as a photomultiplier can acquire image data (radiation image data). It is possible to output a visible image to a photosensitive material or CRT based on the image data. Although a CR apparatus is a digital imaging apparatus, since it requires an image formation process, that is, reading by secondary excitation, it can be called an indirect imaging apparatus. The reason why this apparatus is called an "indirect" apparatus is that it cannot display an acquired captured image (radiation image) in real time like a technique of acquiring the above radiation image as an analog photograph (to be referred to as an "analog photography technique" hereinafter).

There has recently been developed an apparatus which acquires a digital radiation image by using, as an image receiving unit, a photoelectric conversion unit (an imaging device such as a CCD) having pixels, each including a minute photoelectric conversion element and a switching element, arrayed in the form of a matrix. Such apparatuses are disclosed as radiation imaging apparatuses, each having a phosphor formed on a CCD or amorphous silicon two-dimensional imaging device, in U.S. Pat. Nos. 5,418,377, 5,396,072, 5,381,014, 5,132,539, and 4,810,881. This apparatus can display an acquired radiation image in real time and hence can be called a direct digital imaging apparatus.

In this case, an indirect or direct digital imaging apparatus is advantageous over an analog photography technique in that, for example, it can eliminate the need to use films, increase the amount of information acquired by image processing, and make a database. A direct digital imaging apparatus is advantageous over an indirect digital imaging apparatus in promptness or the like. The advantage of promptness, in particular, is that it is possible to, for example, instantly display a radiation image obtained by radiation imaging on the spot. That is, for example, this advantage is effective in an emergent medical situation.

In a direct digital imaging apparatus using an imaging device such as a CCD as an image receiving unit like that described above, the gain of each pixel of the imaging device is not constant. For this reason, in order to generate a uniform output image relative to an input image to the imaging device, it is necessary to perform gain correction for each pixel. Imaging for gain correction is called calibration, which is generally performed by the user at predetermined intervals. More specifically, first of all, the gain of each pixel of the imaging device changes with time due to the influences of usage environment conditions and the like. To acquire a high-quality output image, therefore, it is preferable to perform proper calibration for each startup of the imaging apparatus in accordance with the corresponding situation.

In calibration, first of all, the apparatus irradiates the entire effective imaging area of the imaging device with radiation upon removing any object (to be referred to as a "foreign substance" hereinafter) which makes it difficult to irradiate a radiation detector with a uniform dose of radiation. The apparatus stores the image obtained at this time (to be referred to as a "gain image" hereinafter). An object is then placed, and the apparatus performs actual radiation imaging (clinical imaging). The apparatus performs correction (to be referred to as "gain correction" hereinafter) of variation in the gain of each pixel of the image (clinical image) obtained by this operation by using the gain image stored in advance. Assume that when performing gain correction, the apparatus has captured a gain image with an improper dose of radiation or in the presence of a foreign substance. In this case, the apparatus may not properly correct the captured image by gain correction.

Japanese Patent Laid-Open Nos. 2001-351091 and 2010-12105 disclose a technique of determining whether a gain image is proper by comparing it with a gain image properly captured in the past.

If, however, a foreign substance which is mixed at the time of imaging operation is a low radiation attenuating substance, corresponding data is buried in noise according to conventional techniques. This makes it difficult to properly discriminate whether the imaging operation has been performed with the foreign substance being mixed.

SUMMARY OF THE INVENTION

According to some embodiment of the present invention, there is provided a radiation imaging system including an X-ray sensor with a plurality of sensor chips disposed next to each other and an image processing apparatus which performs abnormality determination concerning a white image obtained by irradiating the X-ray sensor with X-rays without any object disposed between the X-ray sensor and an X-ray generator, the system comprising: an area acquisition unit configured to acquire information of partial areas of the white image which respectively correspond to the plurality of sensor chips; a distribution acquisition unit configured to acquire distribution information representing variation in pixel value for each of the acquired partial areas; and a determination unit configured to determine, based on the distribution information, whether abnormality is included in the white image.

According to another embodiment of the present invention, there is provided an image processing apparatus which performs abnormality determination for a white image obtained by irradiating a digital X-ray imaging apparatus with X-rays without through an object, the apparatus comprising: a correction unit configured to correct X-ray tube shading of the white image; and a determination unit configured to determine, based on pixel values of the corrected white image, whether abnormality is included in the white image.

According to still another embodiment of the present invention, there is provided an image processing apparatus which performs abnormality determination for a white image obtained by irradiating a digital X-ray imaging apparatus with X-rays without through an object, the apparatus comprising: a histogram acquisition unit configured to acquire a histogram for each of a plurality of determination areas as a target for which presence of abnormality is to be determined; and a determination unit configured to determine, based on each of the histograms and a reference histogram, whether abnormality is included in each of the determination areas.

According to yet another embodiment of the present invention, there is provided an image processing apparatus which performs abnormality determination for a white image obtained by irradiating a digital X-ray imaging apparatus with X-rays without through an object, the apparatus comprising: a division unit configured to divide the white image into a plurality of small areas based on pixel values of the white image; a distribution acquisition unit configured to acquire distribution information representing variation in pixel value for each of the small areas; and a determination unit configured to determine, based on the distribution information, whether abnormality is included in the white image.

Further features of the embodiments of the present invention will become apparent from the following description of exemplary embodiments (with reference to the attached drawings).

DESCRIPTION OF THE EMBODIMENTS

The embodiments of the present invention will be exemplarily described in detail below with reference to the accompanying drawings. Note that the constituent elements described in the embodiments are merely examples. The technical scope of the present invention is determined by the scope of claims and is not limited by the following individual embodiments.

First Embodiment

Figure 1A:
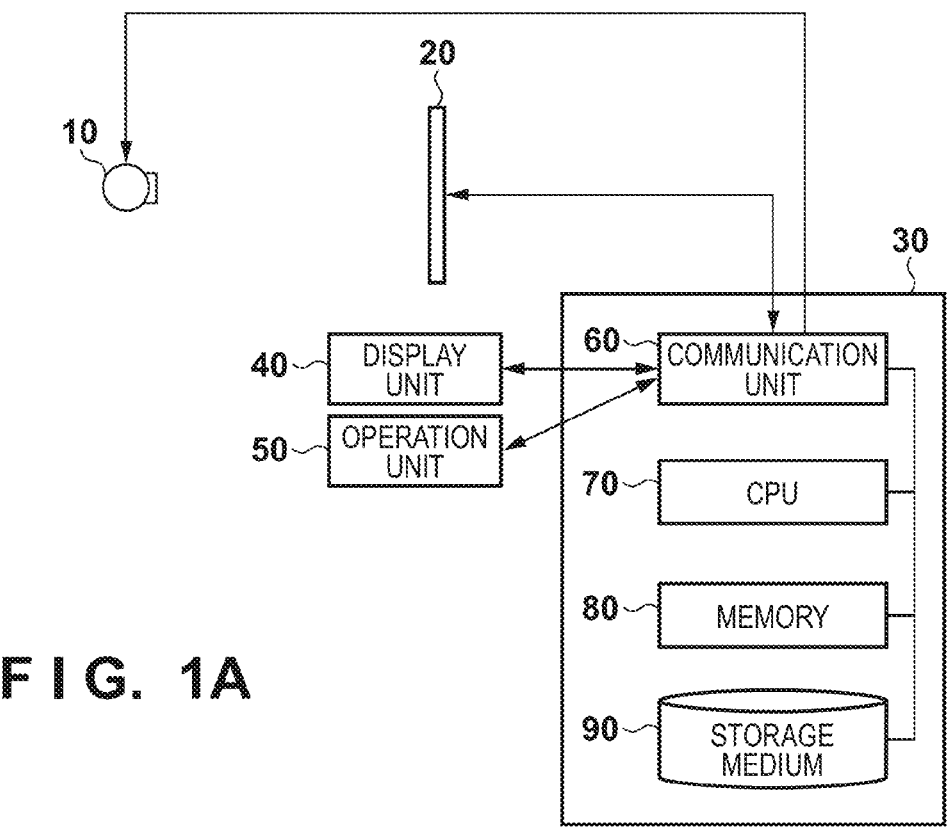
FIG. 1A is a view for explaining the arrangement of an image processing apparatus according to the first embodiment.
Figure 1B:
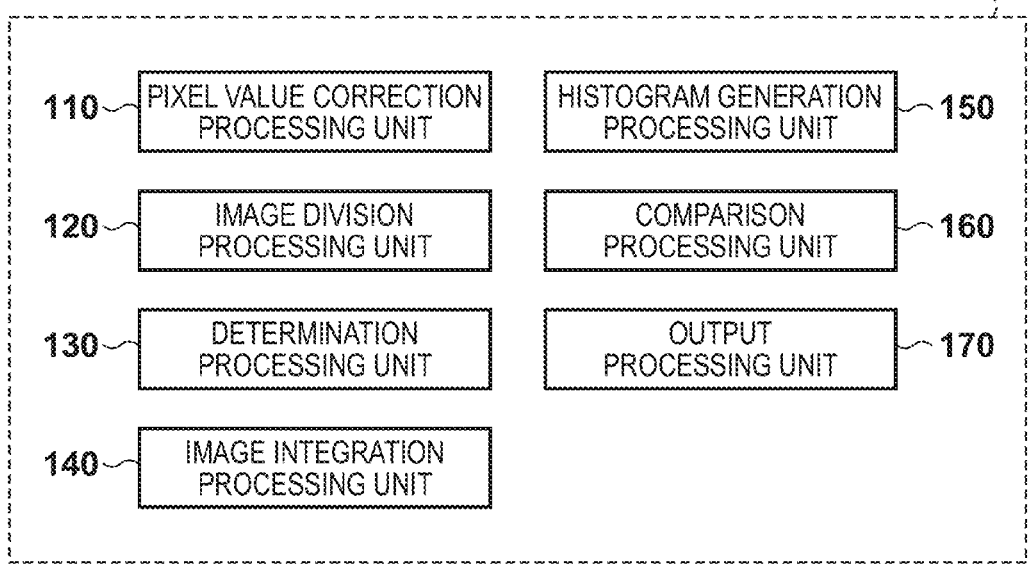
FIG. 1B is a block diagram for explaining the functional arrangement of the image processing apparatus according to the first embodiment.

FIGS. 1A and 1B are views for explaining the arrangement of an image processing apparatus 30 according to an embodiment of the present invention. A radiation generator 10 generates radiation. A radiation detector 20 detects the radiation generated by the radiation generator 10 and generates image data. A radiation imaging system includes the radiation generator 10, the radiation detector 20, and the image processing apparatus 30. The radiation detector 20 generates image data by converting the radiation received by radiation detection elements constituting the radiation detector 20 into an analog electrical signal and then converting it into a digital signal. The radiation detector 20 transmits the generated image data to the connected image processing apparatus 30. The radiation detector 20 and the image processing apparatus 30 are connected to each other via a wired or wireless network. The image processing apparatus 30 can acquire image data from the radiation detector 20 via the network.

The image processing apparatus 30 includes a communication unit 60 (I/O unit) which performs transmission/reception and the like of data inside and a CPU 70 (control unit) which controls the overall operation of the image processing apparatus 30. The image processing apparatus 30 also includes a memory 80 from/in which programs and data used for arithmetic processing by the CPU 70 are read/written and a storage medium 90 which stores and saves image data and the like. A display unit 40 which displays image data, processing results on the image data, and the like and an operation unit 50 for accepting operation by the user are connected to the image processing apparatus 30. The apparatus switches the display on the user interface (UI) on the display unit 40 in accordance with an operation input from the operation unit 50, and an operation input from the user and control information from the CPU 70 (control unit) are transmitted to the radiation generator 10 and the radiation detector 20 via the communication unit 60 (I/O unit).

The operation of the image processing apparatus 30 which performs calibration will be described next. The operator inputs operation for starting calibration by using the operation unit 50. In accordance with this operation input, the display unit 40 switches to a UI display mode for capturing a gain image. The CPU 70 (control unit) generates control information indicating the irradiation timing for radiation. The communication unit 60 transmits the control information generated by the CPU 70 (control unit) to the radiation generator 10. The radiation generator 10 generates radiation in accordance with the received irradiation timing for control information so as to irradiate all the radiation detection elements (radiation detection pixels) of the radiation detector 20 with the radiation. Upon receiving the radiation, the radiation detector 20 converts the radiation received by each radiation detection element (radiation detection pixel) into an analog electrical signal, and then converts the analog electrical signal into a digital signal. The radiation detector 20 transmits the digital signal as image data to the image processing apparatus 30. The image processing apparatus 30 performs foreign substance detection processing (FIG. 2) (to be described later) for the image data received from the radiation detector 20, and transmits the processing result to the display unit 40. The display unit 40 displays the processing result received from the image processing apparatus 30.

(Foreign Substance Detection Processing)

Figure 2:
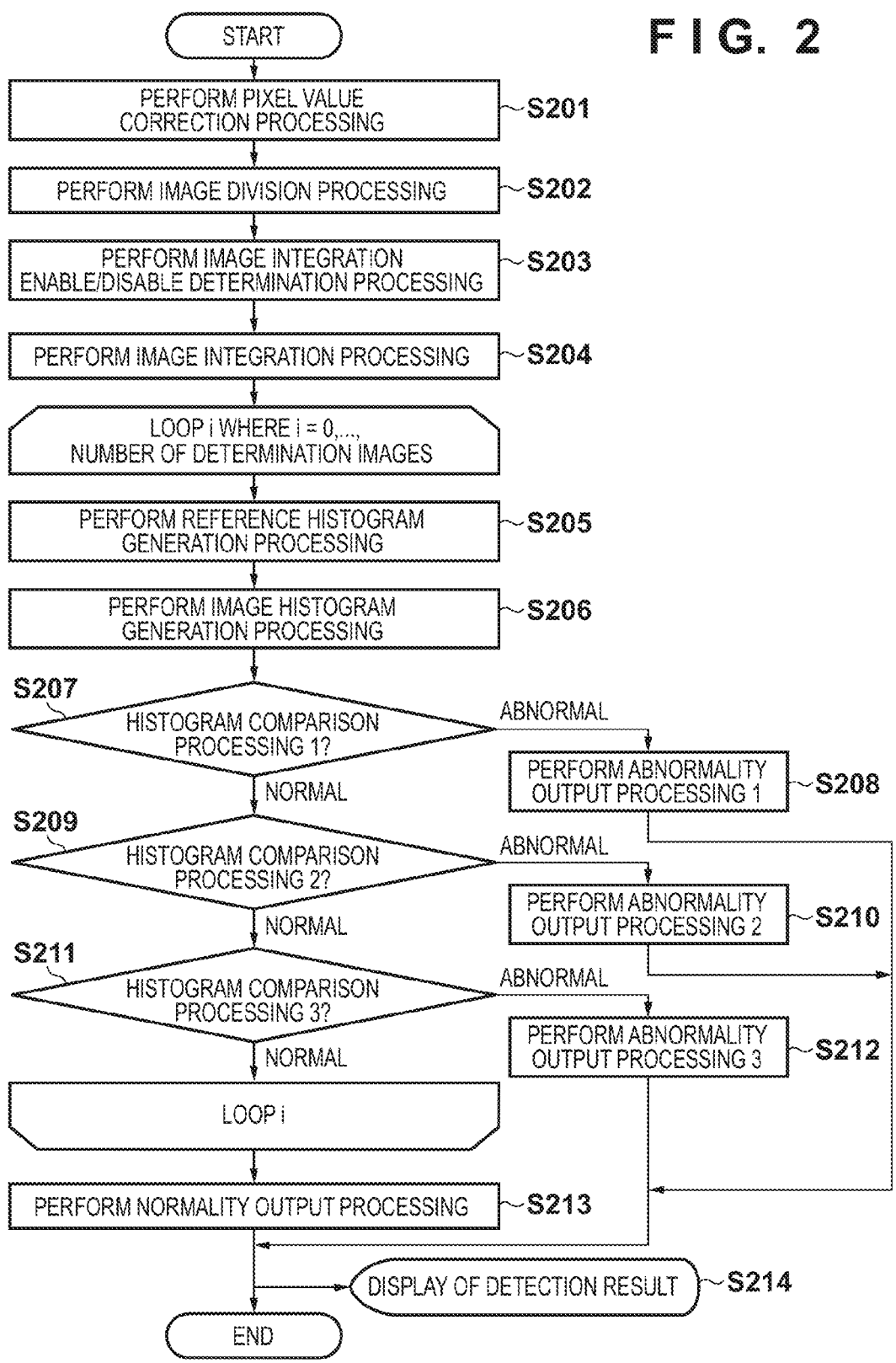
FIG. 2 is a flowchart for explaining a procedure for image processing according to the first embodiment.
Figure 7:
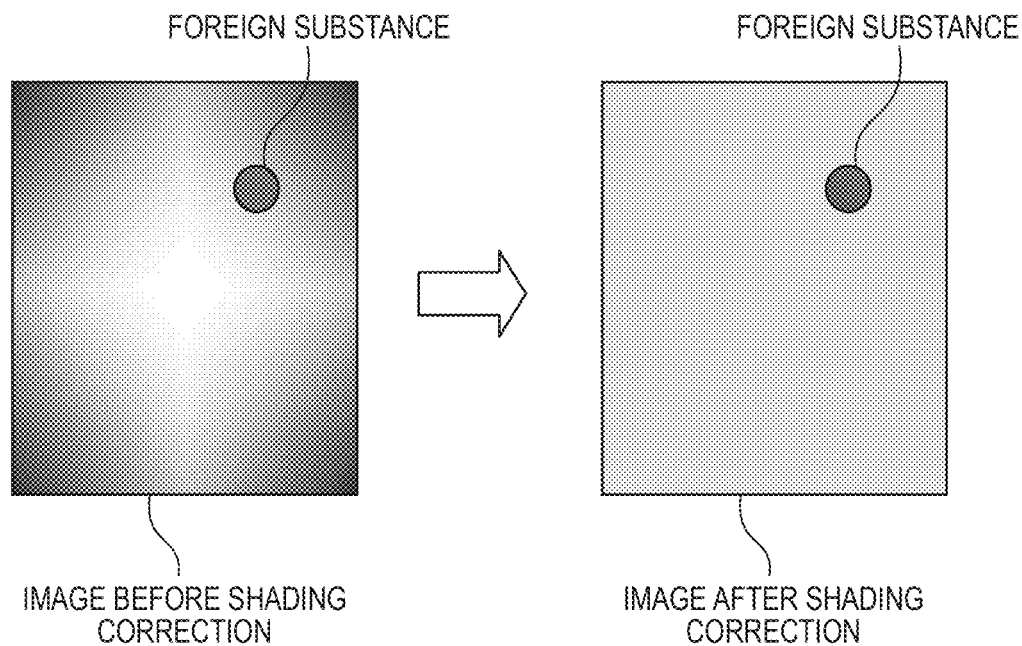
FIG. 7 is a view for explaining shading correction.

A procedure for image processing (foreign substance detection processing) according to the first embodiment of the present invention will be described with reference to FIG. 2. FIG. 1B is a block diagram showing the functional arrangement of the image processing apparatus 30 which executes foreign substance detection processing. In step S201, a pixel value correction processing unit 110 performs shading correction based on the distance from the radiation source of the radiation generator 10 to each radiation detection element (radiation detection pixel) of the radiation detector 20, as shown in FIG. 7. The pixel value correction processing unit 110 obtains an approximate expression from a bivariate quadratic polynomial (equation (1)) by the least-square method. The pixel value correction processing unit 110 then performs correction by adding the average value of the pixel values of the image before correction to the difference between each radiation detection pixel and the pixel value based on the approximate expression (equation (2)). The image obtained in step S201 will be referred to as a corrected image hereinafter.

$$V_{fit}(x,y) = a_1 x^2 + a_2 x + a_3 x \cdot y + a_3 y^2 + a_4 y + a_5 \quad (1)$$

where x and y respectively represent coordinates on the x- and y-axes of the image, $V_{fit}(x, y)$ represents pixel values on the x- and y-coordinates, and $a_1, a_2, \ldots, a_5$ represent coefficients for the respective terms which are obtained by the least-square method.

$$V_c(x,y) = V_o(x,y) - V_{fit}(x,y) + \overline{V}_o \quad (2)$$

where $V_c(x, y)$ represents pixel values on the x- and y-coordinates after correction, $V_o(x, y)$ represents pixel values on the x- and y-coordinates before correction, and $\overline{V}_o$ represents the average value of the pixel values of the image before correction.

In step S202, an image division processing unit 120 divides the corrected image obtained by the previous pixel value correction processing in step S201 into images (determination images) in a plurality of areas for determining the presence/absence of abnormality. In this case, the image division processing unit 120 may divide the corrected image into fixed-size areas or can divide the corrected image upon changing the size of each divided determination image in accordance with the detection accuracy based on the mechanical/electrical characteristics of the radiation detector 20. For example, in the high-resolution radiation detector 20 having high detection accuracy, the image division processing unit 120 divides the corrected image into determination images with a small image size (first image size). In the low-resolution radiation detector 20 having low detection accuracy, the image division processing unit 120 divides the corrected image into determination images with a large image size (second image size) larger than the first image size. Even when using the radiation detector 20 having low detection accuracy, it is possible to increase the number of samples (pixels) within each determination image to be used for comparison processing by increasing the size of each divided area. This makes it possible to perform more stable statistical processing.

Images in a plurality of areas divided by the image division processing unit 120 will be referred to as a determination image group, and an image in one area of the determination image group will be referred to as a determination image which is a determination target for which the presence/absence of abnormality is to be determined.

If the number of pixels included in each determination image obtained by the image division processing unit 120 is small, noise may have a great influence on the accuracy of the histogram obtained by the subsequent processing (steps S205 and S206). For this reason, the apparatus determines determination images which can be integrated in step S203 (image integration enable/disable determination processing). In step S204 (image integration processing), the apparatus integrates the areas determined as being allowed to be integrated in step S203.

Figure 8:
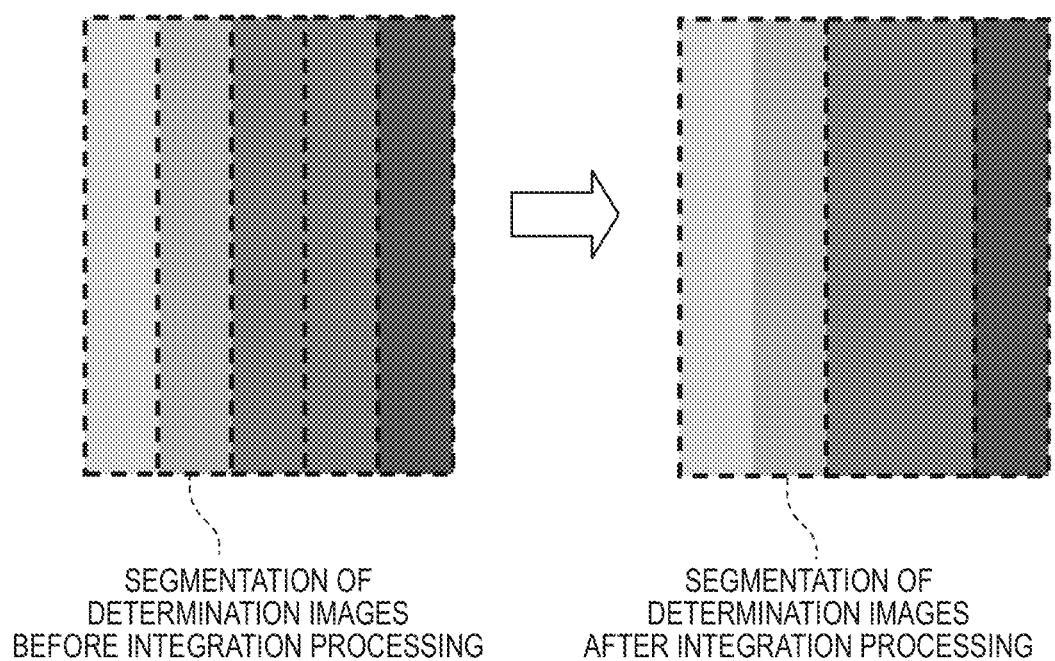
FIG. 8 is a view for explaining image integration processing.

First of all, in step S203, a determination processing unit 130 obtains the feature of each of adjacent determination images as shown in FIG. 8, and determines that it is possible to integrate the adjacent determination images, if the features fall within a threshold range. In contrast, if the features exceed the threshold range, the determination processing unit 130 determines that it is not possible to integrate the adjacent determination images. For example, in this determination processing, the average value of the pixel values of one of adjacent determination images is set as a feature, and the range defined by the average value of the pixel values of the other determination image±a standard deviation is set as a threshold range. In this case, the determination processing unit 130 determines whether it is possible to integrate the adjacent determination images with each other by determining whether the feature of one determination image falls within the threshold range.

In step S204, an image integration processing unit 140 integrates the determination images determined as being allowed to be integrated in accordance with the determination result obtained by determination processing in step S203. The image group integrated by the image integration processing unit 140 will be referred to as a determination image group hereinafter. The determination image group constituted by a plurality of determination images is an area (reference area) as a reference for the generation of a reference histogram. It is possible to generate an accurate reference histogram by increasing the number of pixel samples of images in the reference area.

The apparatus then generates and compares a histogram as a reference (to be referred to as a reference histogram hereinafter) and a histogram of each determination image (to be referred to as a determination image histogram hereinafter) for each determination image group.

In step S205, a histogram generation processing unit 150 (acquisition unit) acquires information (reference information) representing variation in pixel value for each reference area (determination image group). The histogram generation processing unit 150 (acquisition unit) then generates a histogram as a reference (to be referred to as a reference histogram hereinafter) indicating the relationship between pixel values and frequencies by using the acquired information (reference information) representing variation in pixel value. The histogram generation processing unit 150 (acquisition unit) generates a reference histogram from the average value of the pixel values of the determination image and the standard deviation by adding up pixel counts to a normal probability distribution (equation (3)). Note that a Poisson distribution may be used instead of a normal distribution.

$$H_s(v) = \frac{N}{\sqrt{2\pi\sigma^2}} \exp\left(-\frac{(v-\mu)^2}{2\sigma^2}\right) \quad (3)$$

where v is a pixel value, $H_s(v)$ is the frequency of the pixel value v on the histogram, N is the pixel count of the determination image, σ is the standard deviation of the pixel values of the determination image, and μ is the average value of the pixel values of the determination image.

In step S206, the histogram generation processing unit 150 acquires information (distribution information) representing the distribution of variations in pixel values of the determination image as a determination target for which the presence/absence of abnormality is to be determined. The histogram generation processing unit 150 then generates a histogram of the determination image (to be referred to as a determination image histogram hereinafter) indicating the relationship between pixel values and frequencies by using information (distribution information) representing the acquired distribution of variation in pixel value and equation (3) described above.

A comparison processing unit 160 determines whether the determination image includes abnormality by comparison processing using the reference information and the distribution information. In comparison processing, the comparison processing unit 160 determines the presence/absence of abnormality in the determination image by comparing the reference histogram with the determination image histogram. The comparison processing unit 160 executes comparison processing 1, comparison processing 2, and comparison processing 3 (to be exemplified below) as processing in steps S207, S209, and S211. In the following description, comparison processing 1 is executed as processing in step S207, comparison processing 2 is executed as processing in step S209, and comparison processing 3 is executed as processing in step S211. However, the execution order of these types of processing is not limited to this. Comparison processing 1, comparison processing 2, and comparison processing 3 may be executed in random order.

(Comparison Processing 1)

In step S207, the comparison processing unit 160 compares the number of local maximum values of the reference histogram with the number of local maximum values of the determination image histogram. If the numbers of local maximum values differ, the comparison processing unit 160 determines that the determination image is abnormal. If the numbers of local maximum values are equal, the comparison processing unit 160 determines that the determination image is normal.

Figure 4A:
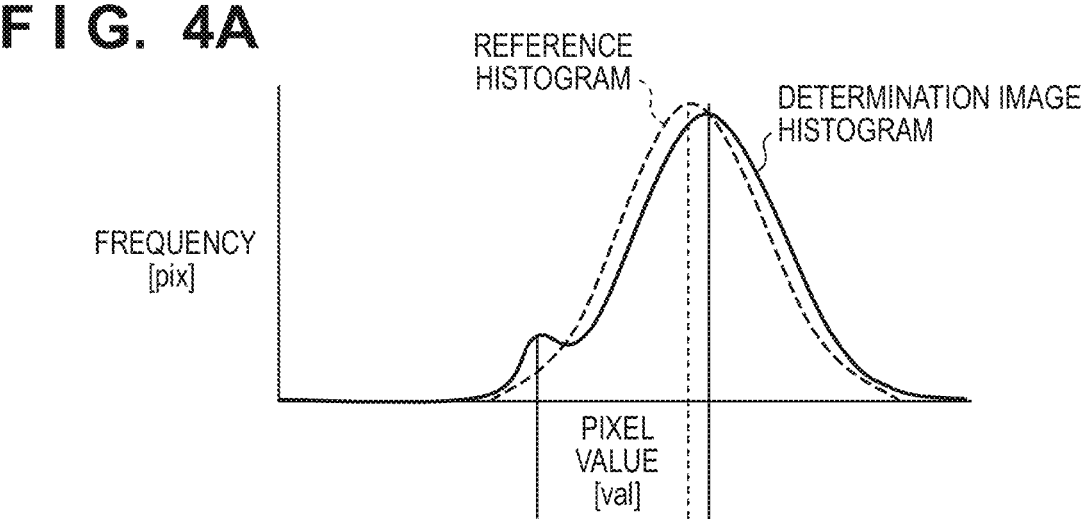
FIGS. 4A and 4B are graphs for explaining comparison processing 1.
Figure 4B:
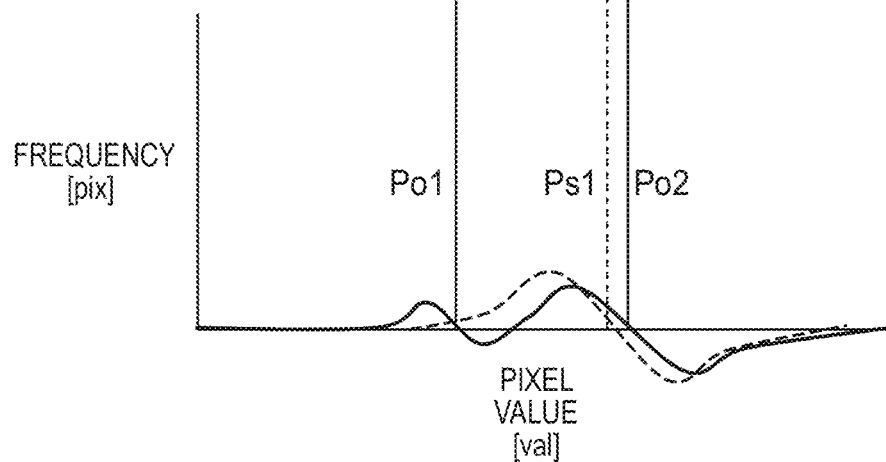

As a method of calculating the number of local maximum values, for example, the comparison processing unit 160 smoothes a histogram by a moving average, Gaussian filter, or the like, and can obtain the number of times of switching from a positive value to a negative value by first derivation as the number of local maximum values. FIG. 4A exemplifies a determination image histogram with a foreign substance and a reference histogram approximated by a normal distribution. FIG. 4B exemplifies differential results on the histograms. As shown in FIG. 4A, the determination image histogram decreases in pixel value due to a foreign substance and has two local maximum values concerning an area without any foreign substance and an area with a foreign substance. In contrast to this, the reference histogram is a normal histogram having a standard deviation relative to the average value of the determination image, and hence has only one local maximum value. Applying differential processing to the determination image histogram and the reference histogram will obtain a graph like that shown in FIG. 4B. It is possible to acquire the numbers of local maximum values by counting the numbers of times of changing from a positive value to a negative value in this graph. Referring to FIG. 4B, the determination image histogram has two local maximum values $P_{o1}$ and $P_{o2}$. The reference histogram has only one local maximum value $P_{s1}$. Since the numbers of local maximum values differ, it is clear that the determination image includes a foreign substance. If the number of local maximum values acquired from the determination histogram (distribution information) is equal to the number of local maximum values acquired from the reference histogram (reference information), the comparison processing unit 160 determines that the determination image is normal. If the number of local maximum values acquired from the determination histogram differs from the number of local maximum values acquired from the reference histogram (reference information), the comparison processing unit 160 determines that the determination image includes abnormality.

If the comparison processing unit 160 determines in comparison processing 1 in step S207 that the determination image is abnormal, the process advances to step S208. An output processing unit 170 outputs the abnormality determination result in comparison processing 1 (abnormality output processing 1). The output processing unit 170 can control the display unit 40 to display, as abnormality output processing 1, for example, the reference histogram and the determination image histogram in FIG. 4A, the differential results on the histograms in FIG. 4B, and the comparison result on the numbers of local maximum values (step S214). The output processing unit 170 can also control the display unit 40 to display, as abnormality output processing 1, a message for notifying the operator of the determination of abnormality (step S214).

If the comparison processing unit 160 determines in comparison processing 1 in step S207 that the determination image is normal, the process advances to comparison processing 2 in step S209.

(Comparison Processing 2)

In step S209, if the number of pixels of the determination image histogram which have pixel values equal to or smaller than a pixel value threshold exceeds the total number of pixels of the reference histogram which have pixel values equal to or smaller than the pixel value threshold, the comparison processing unit 160 determines that the determination image is abnormal. If the number of pixels of the determination image histogram which have pixel values equal to or smaller than the pixel value threshold is equal to or smaller than a pixel count threshold, the comparison processing unit 160 determines that the determination image is normal.

For example, the comparison processing unit 160 acquires the average value and standard deviation of the pixel values of a determination image, and then acquires a pixel value threshold from the acquired average value and standard deviation by calculation of equation (4).

$$B_v = \mu - A_v \cdot \sigma \quad (4)$$

where $B_v$ is a pixel value threshold, μ is the average value of the pixel values of the determination image, σ is the standard deviation of the pixel values of the determination image, and $A_v$ is a coefficient. Note that the coefficient $A_v$ may be an arbitrary numeral value but is preferably about 2 to 4 when the reference histogram is approximated by a normal distribution.

The comparison processing unit 160 then acquires the total number of pixels (pixel count threshold) of the reference histogram which have pixel values equal to or smaller than the pixel value threshold $B_v$ by using equation (5).

$$B_{pix} = A_{pix} \cdot P_s \quad (5)$$

where $B_{pix}$ represents a pixel count threshold, $P_s$ represents the total number of pixels (pixel count) of the reference histogram which have pixel values equal to or smaller than the pixel value threshold $B_v$, and $A_{pix}$ represents a coefficient. As the coefficient $A_{pix}$, for example, a value of 1.0 or more can be used. In addition, it is possible to set the coefficient $A_{pix}$ by statistically obtaining a value that can be taken in an implementation system or apparatus without any foreign substance.

Figure 5:
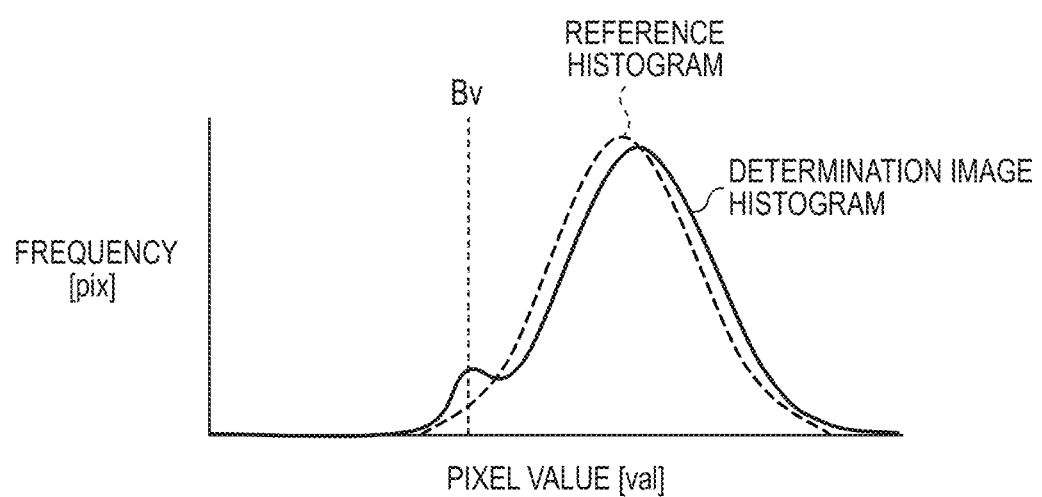
FIG. 5 is a graph for explaining comparison processing 2.

As shown in FIG. 5, the number of pixels, of the determination image histogram with a foreign substance, which have pixel values equal to or smaller than the pixel value threshold $B_v$ exceeds the number of pixels (pixel count threshold) of the reference histogram. Properly setting the coefficient $A_{pix}$ which obtains a pixel count threshold makes it possible to accurately determine whether the determination image is abnormal or normal.

If the number of pixels of the determination histogram (distribution information) which have pixel values equal to or smaller than the threshold is equal to or smaller than the number of pixels of the reference histogram (reference information) which have pixel values equal to or smaller than threshold, the comparison processing unit 160 determines that the determination image is normal. In contrast to this, if the number of pixels of the determination histogram which have pixel values equal to or smaller than the threshold exceeds the number of pixels of the reference histogram which have pixel values equal to or smaller than pixel value threshold, the comparison processing unit 160 determines that abnormality is included in the determination image.

If the comparison processing unit 160 determines in comparison processing 2 in step S209 that the determination image is abnormal, the process advances to step S210. The output processing unit 170 outputs the abnormality determination result in comparison processing 2 (abnormality output processing 2). For example, the output processing unit 170 can control the display unit 40 to display the histograms in FIG. 5, the pixel count threshold $B_{pix}$ on the reference histogram, and the comparison result on the number of pixels of the determination image histogram (step S214). The output processing unit 170 can also control the display unit 40 to display a message for notifying the operator of the determination of abnormality as abnormality output processing 2 (step S214).

If the comparison processing unit 160 determines in comparison processing 2 in step S209 that the determination image is normal, the process advances to comparison processing 3 in step S211.

(Comparison Processing 3)

In step S211, the comparison processing unit 160 acquires a coefficient (correlation coefficient) representing the correlation between the reference histogram and the determination image histogram by using equation (6). If the correlation coefficient obtained by equation (6) is equal to or larger than a threshold, the comparison processing unit 160 determines that the determination image is normal. If the correlation coefficient is less than the threshold, the comparison processing unit 160 determines that the determination image is abnormal. It is possible to set a threshold by statistically obtaining a value that can be taken in an implementation system or apparatus without any foreign substance.

$$C = \frac{\sum_{i=V_{min}}^{V_{max}} (H_s(i) - \mu)(H_o(i) - \mu)}{\sqrt{\sum_{i=V_{min}}^{V_{min}} (H_s(i) - \mu)^2} \sqrt{\sum_{i=V_{min}}^{V_{max}} (H_0(i) - \mu)^2}} \quad (6)$$

where C is a correlation coefficient, Vmax and Vmin are the maximum and minimum values of a determination image, Hs(i) is the frequency of a pixel value i on a reference histogram, Ho(i) is the frequency of a pixel value i on the determination image histogram, and μ is the average value of the pixel values of the determination image. Equation (6) represents the value obtained by dividing each covariance by a corresponding standard deviation.

In comparison processing 3 in step S211, if the comparison processing unit 160 determines that the determination image is abnormal, the process advances to step S212. The output processing unit 170 outputs the abnormality determination result obtained in comparison processing 3 (abnormality output processing 1). The output processing unit 170 can control the display unit 40 in abnormality output processing 3 so as to display, for example, the comparison result on the correlation coefficients (step S214). The output processing unit 170 can also control the display unit 40 in abnormality output processing 3 so as to display a message for notifying the operator of the determination of abnormality (step S214).

The execution order of comparison processing results 1, 2, and 3 in steps S207, S209, and S211 is not limited to that described above. When the execution order of comparison processing results 1, 2, and 3 changes, the execution order of abnormality output processing 1, abnormality output processing 2, and abnormality output processing 3 corresponding to the comparison processing results is also changed in accordance with the execution order of comparison processing results 1, 2, and 3.

If the comparison processing unit 160 determines in all comparison processing 1, comparison processing 2, and comparison processing 3 in steps S207, S209, and S211 that the determination image is normal, the process advances to step S213. The output processing unit 170 outputs normality determination results obtained in comparison processing 1, comparison processing 2, and comparison processing 3 (normality output processing). The output processing unit 170 can also control the display unit 40 to display, as the processing results obtained in comparison processing 1, comparison processing 2, and comparison processing 3, a message for notifying the operator of the determination of normality. Alternatively, in order to reduce the cumbersomeness of operator's check on notification, it is possible to notify the operator in abnormality output processing 1, abnormality output processing 2, and abnormality output processing 3 only when the determination image is abnormal without outputting any message when the comparison processing unit 160 determines that the determination image is normal. In step S214, the output processing unit 170 controls the display unit 40 to display the comparison processing results obtained in comparison processing 1, comparison processing 2, and comparison processing 3. According to this embodiment, it is possible to detect abnormality (foreign substance) indicating a pixel value similar to noise included in image data. This makes it possible to properly detect a foreign substance exhibiting low radiation attenuation even if a gain image is captured with the foreign substance being mixed.

Second Embodiment

Figure 3A:
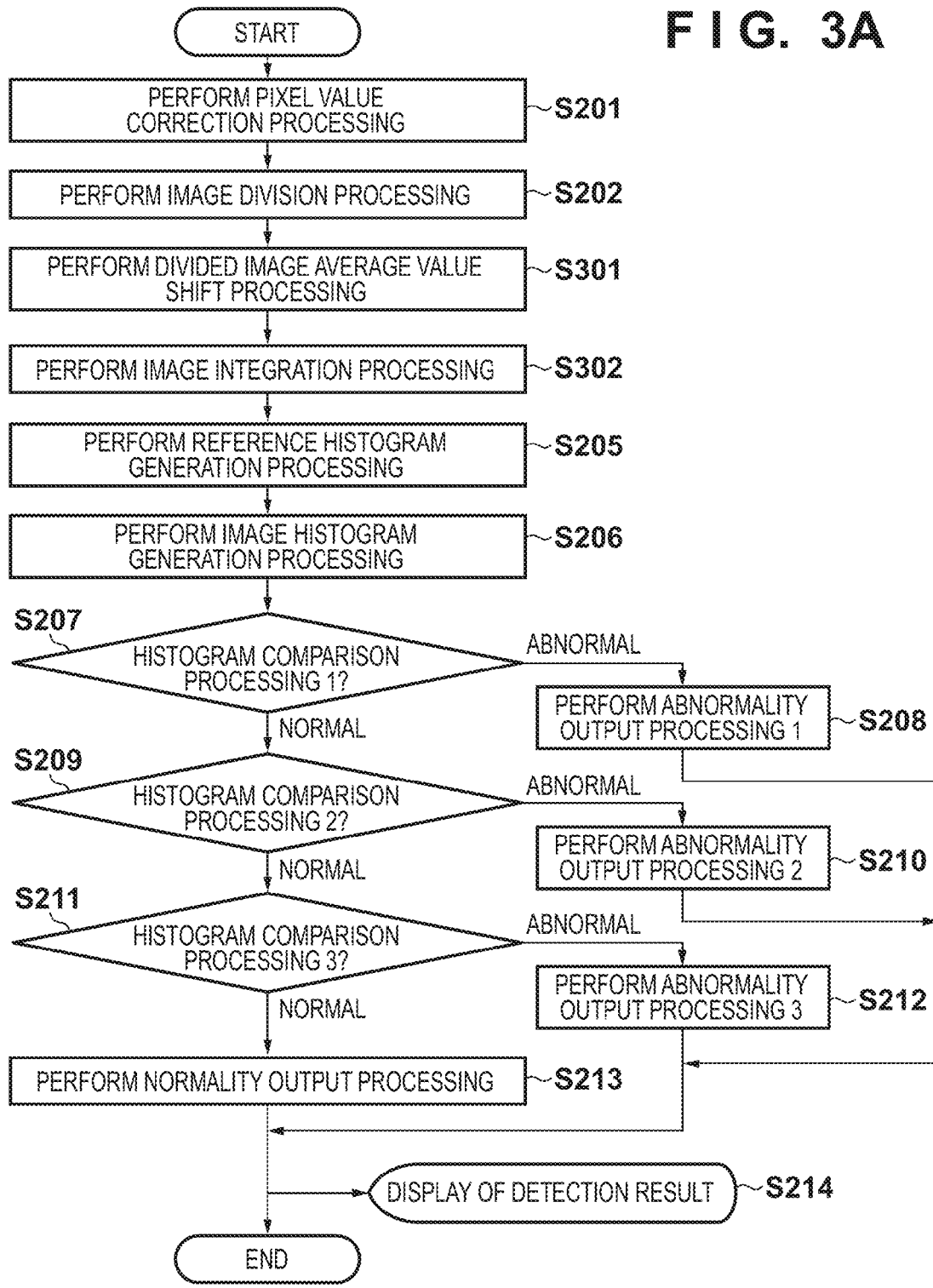
FIG. 3A is a flowchart for explaining a procedure for image processing according to the second embodiment.
Figure 3B:
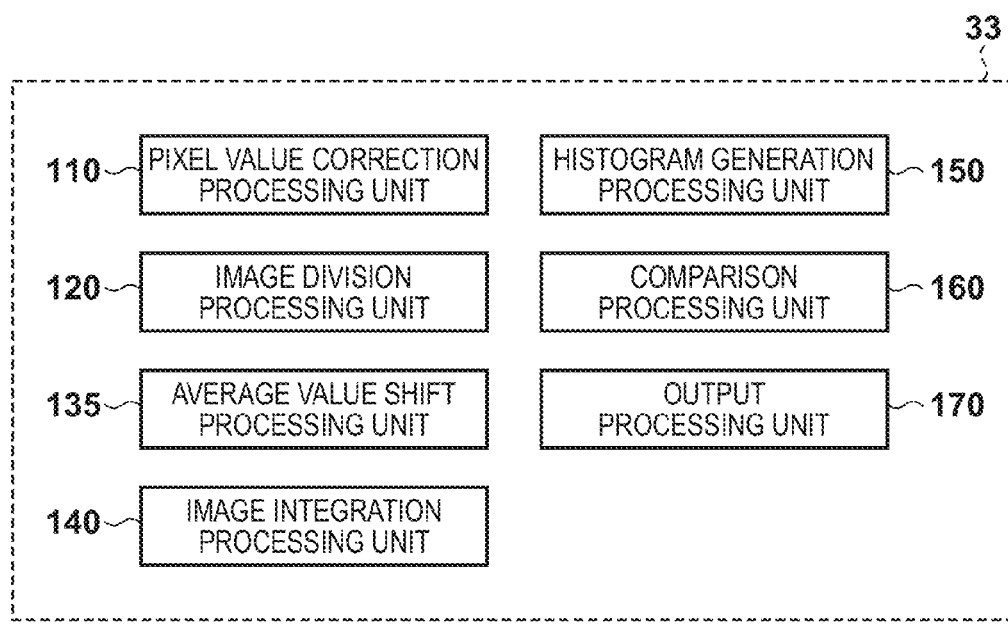
FIG. 3B is a block diagram for explaining the functional arrangement of an image processing apparatus according to the second embodiment.

A procedure for image processing (foreign substance detection processing) according to the second embodiment of the present invention will be described with reference to FIG. 3A. The same step numbers as in FIG. 2 denote the same processes in FIG. 3A, and a description of them will be omitted. FIG. 3B is a block diagram showing the functional arrangement of an image processing apparatus 33 according to this embodiment. The image processing apparatus 33 differs from that of the first embodiment in that it includes an average value shift processing unit 135 instead of the determination processing unit 130 (FIG. 1B). In step S201, a pixel value correction processing unit 110 corrects a pixel value by using equations (1) and (2) in the same manner as in the first embodiment. In step S202, an image division processing unit 120 divides the corrected image previously obtained in step S201 into a plurality of areas.

Figure 6:
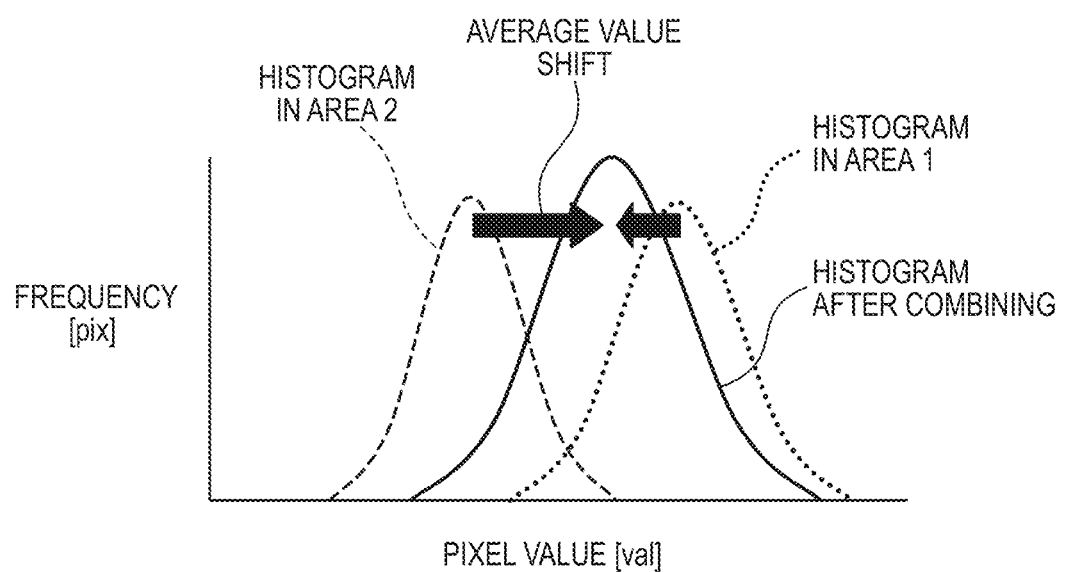
FIG. 6 is a graph for explaining an average value shift processing function.

In step S301, the average value shift processing unit 135 corrects (shifts) the average value of the pixel values of a determination image so as to match with the average value of the pixel values of the corrected image before division by using equation (7), as shown in FIG. 6.

$$V'_{cc}(x,y) = V_{cc}(x,y) - \mu_{cc} + \mu_{c} \quad (7)$$

where x and y respectively represent coordinates on the x- and y-axes of the image, $V'_{cc}(x, y)$ represents pixel values on the x- and y-coordinates of the determination image after an average value shift, $V_{cc}(x, y)$ represents pixel values on the x- and y-coordinates of the determination image, $\mu_{cc}$ represents the average pixel value of the determination image, and $\mu_{c}$ represents the average pixel value of the corrected image.

In step S302, an image integration processing unit 140 integrates all the determination images after the average value shift in step S301 into one image. When acquiring a value like the frequency distribution or standard deviation of a histogram, it is possible to acquire a more stable statistical value by increasing the number of samples (the number of pixels) of a reference area. It is possible to increase the number of samples (the number of pixels) of a reference area by shifting the average value of the determination image so as to equalize the features (the average values of pixel values) of determination images in the processing of step S302. This makes it possible to perform more stable statistical processing.

The one image integrated in step S302 corresponds to a determination image group in the first embodiment, and the determination images constituting the one integrated image correspond to determination images in the first embodiment. The subsequent processing from reference histogram generation processing (step S205) to detection result display processing (step S214) is the same as that in the first embodiment.

According to this embodiment, it is possible to detect abnormality (foreign substance) indicating a pixel value similar to noise included in image data. This makes it possible to properly detect a foreign substance exhibiting low radiation attenuation even if a gain image is captured with the foreign substance being mixed.

Third Embodiment

Each embodiment described above has exemplified the arrangement configured to execute comparison processing 1, comparison processing 2, and comparison processing 3 in random order. In order to increase the processing speed of a comparison processing unit 160, it is possible to perform comparison processing by performing any one of comparison processing 1, comparison processing 2, and comparison processing 3 or a combination of two types of comparison processing (for example, a combination of comparison processing 1 and comparison processing 2, a combination of comparison processing 1 and comparison processing 3, or a combination of comparison processing 2 and comparison processing 3). Note that even when executing a combination of two types of comparison processing, the execution order is random.

When performing calibration, the apparatus switches the display of a user interface (UI) on a display unit 40 in accordance with an operation input from an operation unit 50. The UI of the display unit 40 displays a menu window for allowing to select whether to execute comparison processing by one of comparison processing 1, comparison processing 2, and comparison processing 3, a combination of two types of processing of them, or a combination of three types of processing, namely comparison processing 1, comparison processing 2, and comparison processing 3 in the first and second embodiments. The operator can select any of the above types of processing from the menu screen by operating the operation unit 50. According to this embodiment, it is possible to detect abnormality (foreign substance) indicating a pixel value similar to noise included in image data while increasing the processing speed.

According to the embodiment of the present invention, it is possible to detect abnormality similar to noise included in image data.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-247749, filed Nov. 9, 2012, which is hereby incorporated by reference herein in its entirety.

What is claimed is:

1. A radiation imaging system including an X-ray sensor and an image processing apparatus which performs abnormality determination concerning a correction image obtained by irradiating the X-ray sensor with X-rays without an object to be examined disposed between the X-ray sensor and an X-ray generator, the system comprising:

an area acquisition unit configured to acquire information of partial areas of the correction image;

a distribution acquisition unit configured to acquire distribution information representing variation in pixel value for each of the acquired partial areas;

a determination unit configured to determine that adjacent partial areas can be integrated in a case where the distribution information representing variation for the adjacent partial areas fall within a threshold range, wherein the determination unit determines, based on the distribution information, whether abnormality is included in the correction image; and an integration processing unit configured to integrate the adjacent partial areas based on the determination result.

2. The system according to claim 1, further comprising a correction unit configured to perform shading correction of the correction image,
wherein the determination unit determines, based on pixel values of the correction image having undergone the shading correction, whether the correction image includes abnormality.

3. The system according to claim 1, further comprising a histogram acquisition unit configured to acquire a histogram for each of a plurality of determination areas as a target for which presence/absence of abnormality is to be determined,
wherein the determination unit determines, based on each of the histograms and a reference histogram, whether abnormality is included in each of the determination areas.

4. The system according to claim 1, further comprising a division unit configured to divide the correction image into a plurality of partial areas based on pixel values of the correction image.

5. The system according to claim 4, wherein the division unit divides the image detected by the detection unit into a plurality of determination images for which presence/absence of abnormality is to be determined.

6. The system according to claim 5, wherein the distribution acquisition unit acquires reference information representing a distribution of variation in pixel value of an area as a reference for the image and distribution information representing a distribution of variation in pixel value of the determination image.

7. The system according to claim 6, further comprising a comparison processing unit configured to determine whether abnormality is included in the determination image by comparison processing using the reference information and the distribution information.

8. The system according to claim 7, wherein the comparison processing unit acquires the number of local maximum values of the distribution of variation in pixel value of the reference information and the number of local maximum values of the distribution of variation in pixel value of the distribution information by differential processing for the distributions of variation in pixel value,
determines that the determination image is normal, if the number of local maximum values acquired from the distribution information is equal to the number of local maximum values acquired from the reference information, and
determines that abnormality is included in the determination image, if the number of local maximum values acquired from the distribution information differs from the number of local maximum values acquired from the reference information.

9. The system according to claim 7, wherein the comparison processing unit determines that the determination image is normal, if the number of pixels in the distribution information which have pixel values not more than a threshold is not more than the number of pixels in the reference information which have pixel values not more than the threshold, and
determines that abnormality is included in the determination image, if the number of pixels in the distribution information which have pixel values not more than a threshold exceeds the number of pixels in the reference information which have pixel values not more than the threshold.

10. The system according to claim 7, wherein the comparison processing unit acquires a coefficient indicating a correlation between the distribution of variation in pixel value of the reference information and the distribution of variation in pixel value of the distribution information, and
determines that the determination image is normal, if the coefficient is not less than a threshold, and that abnormality is included in the determination image, if the coefficient is less than the threshold.

11. The system according to claim 5, wherein the determination unit determines that adjacent determination images are configured to be integrated, if features of the adjacent determination images fall within a threshold range, and determines that the adjacent determination images are not configured to be integrated, if the features exceed the threshold range.

12. The system according to claim 11, wherein the integration processing unit integrates the adjacent determination images determined as being allowed to be integrated into an image in the area as the reference.

13. The system according to claim 5, further comprising a correction unit configured to perform shading correction for an image detected by a detection unit,
wherein the division unit divides the corrected image having undergone the shading correction into a plurality of determination images as a target for which presence/absence of abnormality is to be determined.

14. The system according to claim 5, further comprising:
a correction unit configured to perform shading correction for an image detected by a detection unit; and
an average value shift processing unit configured to correct an average value of pixel values of the determination image so as to match with an average value of pixel values of the image having undergone the shading correction,
wherein the integration processing unit integrates the determination images whose average values of pixel values have been corrected into one image as an image in an area as the reference.

15. The system according to claim 7, wherein the distribution acquisition unit generates a reference histogram indicating a relationship between pixel values and frequencies concerning the image in the area as the reference from the reference information and a determination image histogram indicating a relationship between pixel values and frequencies concerning the determination image from the distribution information, and
the comparison processing unit determines whether abnormality is included in the determination image by the comparison processing using the reference histogram and the determination image histogram.

16. The system according to claim 15, further comprising an output processing unit configured to display the reference histogram and the determination image histogram side by side on a display unit.

17. The system according to claim 16, wherein the output processing unit displays a determination result obtained by the comparison processing unit on the display unit.

18. The system according to claim 5, wherein the division unit changes a size of a divided determination image in accordance with detection accuracy of the detection unit.

19. An image processing apparatus which performs abnormality determination for a correction image obtained by irradiating a digital X-ray imaging apparatus with X-rays without an object to be examined, the apparatus comprising:
- a correction unit configured to correct X-ray tube shading of the correction image;
- an area acquisition unit configured to acquire information of partial areas of the correction image, based on pixel values of the correction image;
- a distribution acquisition unit configured to acquire distribution information representing variation in pixel value for each of the acquired partial areas;
- a determination unit configured to determine that adjacent partial areas can be integrated in a case where the distribution information representing variation for the adjacent partial areas fall within a threshold range, wherein the determination unit determines, based on the distribution information, whether abnormality is included in the correction image; and
- an integration processing unit configured to integrate the adjacent partial areas which can be integrated based on the determination result.

20. An image processing apparatus which performs abnormality determination for a correction image obtained by irradiating a digital X-ray imaging apparatus with X-rays without an object to be examined, the apparatus comprising:
- a division unit configured to divide the correction image into a plurality of partial areas based on pixel values of the correction image;
- a distribution acquisition unit configured to acquire distribution information representing variation in pixel value for each of the plurality of partial areas;
- a determination unit configured to determine that adjacent partial areas can be integrated in a case where the distribution information representing variation for the adjacent partial areas fall within a threshold range, wherein the determination unit determines, based on the distribution information, whether abnormality is included in the correction image; and
- an integration processing unit configured to integrate the adjacent partial areas which can be integrated based on the determination result.

21. An image processing method for an image processing apparatus which performs abnormality determination for a correction image obtained by irradiating a digital X-ray imaging apparatus with X-rays without through an object to be examined, the method comprising:
- correcting X-ray tube shading of the correction image;
- acquiring information of partial areas of the correction image, based on pixel values of the correction image;
- acquiring distribution information representing variation in pixel value for each of the acquired partial areas;
- determining that adjacent partial areas can be integrated in a case where the distribution information representing variation for the adjacent partial areas fall within a threshold range, wherein the determining step includes determining, based on the distribution information, whether abnormality is included in the correction image; and
- integrating the adjacent partial areas which can be integrated based on the determination result.

22. An image processing method for an image processing apparatus which performs abnormality determination for a correction image obtained by irradiating a digital X-ray imaging apparatus with X-rays without an object to be examined, the method comprising:
- dividing the correction image into a plurality of partial areas based on pixel values of the correction image;
- acquiring distribution information representing variation in pixel value for each of the plurality of partial areas;
- determining that adjacent partial areas can be integrated in a case where the distribution information representing variation for the adjacent partial areas fall within a threshold range, wherein the determining step includes determining, based on the distribution information, whether abnormality is included in the correction image; and
- integrating the adjacent partial areas which can be integrated based on the determination result.

23. A non-transitory computer-readable storage medium storing a program for causing a computer to serve as each unit of an image processing apparatus which performs abnormality determination for a correction image obtained by irradiating a digital X-ray imaging apparatus with X-rays without an object to be examined, the apparatus comprising:
- a correction unit configured to correct X-ray tube shading of the correction image;
- an area acquisition unit configured to acquire information of partial areas of the correction image, based on pixel values of the correction image;
- a distribution acquisition unit configured to acquire distribution information representing variation in pixel value for each of the acquired partial areas;
- a determination unit configured to determine that adjacent partial areas can be integrated in a case where the distribution information representing variation for the adjacent partial areas fall within a threshold range, wherein the determining step includes determining, based on the distribution information, whether abnormality is included in the correction image; and
- an integration processing unit configured to integrate the partial adjacent areas which can be integrated based on the determination result.

24. A non-transitory computer-readable storage medium storing a program for causing a computer to serve as each unit of an image processing apparatus which performs abnormality determination for a correction image obtained by irradiating a digital X-ray imaging apparatus with X-rays without through an object to be examined, the apparatus comprising:
- a division unit configured to divide the correction image into a plurality of partial areas based on pixel values of the correction image;
- a distribution acquisition unit configured to acquire distribution information representing variation in pixel value for each of the plurality of partial areas;
- a determination unit configured to determine that adjacent partial areas can be integrated in a case where the distribution information representing variation for the adjacent partial areas fall within a threshold range, wherein the determining step includes determining, based on the distribution information, whether abnormality is included in the correction image; and
- an integration processing unit configured to integrate the adjacent partial areas which can be integrated based on the determination result.

25. An image processing apparatus comprising:
- a division unit configured to divide an image detected by a detection unit into a plurality of determination images for which presence/absence of abnormality is to be determined;

a determination unit configured to determine that adjacent determination images are configured to be integrated, if features of the adjacent determination images fall within a threshold range;

an integration processing unit configured to integrate the adjacent determination images determined as being allowed to be integrated;

an acquisition unit configured to acquire reference information representing a distribution of variation in pixel value of the integrated determination images and distribution information representing a distribution of variation in pixel value of the determination image; and a comparison processing unit configured to determine whether abnormality is included in the determination image by comparison processing using the reference information and the distribution information.

26. An image processing method for an image processing apparatus comprising: the method comprising:

dividing an image detected by a detection unit into a plurality of determination images for which presence/absence of abnormality is to be determined;

determining that adjacent determination images are configured to be integrated, if features of the adjacent determination images fall within a threshold range;

integrating the adjacent determination images determined as being allowed to be integrated;

acquiring reference information representing a distribution of variation in pixel value of the integrated determination images and distribution information representing a distribution of variation in pixel value of the determination image; and determining whether abnormality is included in the determination image by comparison processing using the reference information and the distribution information.

27. A non-transitory computer-readable storage medium storing a program for causing a computer to serve as each unit of an image processing apparatus, the apparatus comprising:

a division unit configured to divide an image detected by a detection unit into a plurality of determination images for which presence/absence of abnormality is to be determined;

a determination unit configured to determine that adjacent determination images are configured to be integrated, if features of the adjacent determination images fall within a threshold range;

an integration processing unit configured to integrate the adjacent determination images determined as being allowed to be integrated;

an acquisition unit configured to acquire reference information representing a distribution of variation in pixel value of the integrated determination images and distribution information representing a distribution of variation in pixel value of the determination image; and a comparison processing unit configured to determine whether abnormality is included in the determination image by comparison processing using the reference information and the distribution information.

* * * * *